US008527032B2

(12) United States Patent
Li (10) Patent No.: US 8,527,032 B2
(45) Date of Patent: Sep. 3, 2013

(54) IMAGING SYSTEM AND METHOD OF DELIVERY OF AN INSTRUMENT TO AN IMAGED SUBJECT

(75) Inventor: Dun Alex Li, Salem, NH (US)

(73) Assignee: General Electric Company, Schenectady, NY (US)

( * ) Notice: Subject to any disclaimer, the term of this patent is extended or adjusted under 35 U.S.C. 154(b) by 809 days.

(21) Appl. No.: 12/056,604

(22) Filed: Mar. 27, 2008

(65) Prior Publication Data
US 2008/0287790 A1   Nov. 20, 2008

Related U.S. Application Data

(60) Provisional application No. 60/938,290, filed on May 16, 2007.

(51) Int. Cl.
*A61B 5/05* (2006.01)

(52) U.S. Cl.
USPC ........... 600/424; 600/429; 600/437; 600/439; 600/471; 382/128; 382/130; 382/131

(58) Field of Classification Search
USPC ......... 600/424, 429, 437, 439, 471; 382/128, 382/130, 131
See application file for complete search history.

(56) References Cited

U.S. PATENT DOCUMENTS

| | | | |
|---|---|---|---|
| RE30,397 E | 9/1980 | King | |
| 4,672,963 A | 6/1987 | Barken | |
| 4,706,681 A | 11/1987 | Breyer et al. | |
| 4,722,056 A | 1/1988 | Roberts et al. | |
| 4,750,367 A | 6/1988 | Bernatets | |
| 4,821,731 A | 4/1989 | Martinelli et al. | |
| 4,834,089 A | 5/1989 | Koivukangas et al. | |
| 4,869,256 A | 9/1989 | Kanno et al. | |
| 4,896,673 A | 1/1990 | Rose et al. | |
| 5,099,846 A | 3/1992 | Hardy | |
| 5,135,001 A | 8/1992 | Sinofsky et al. | |
| 5,203,337 A | 4/1993 | Feldman | |

(Continued)

FOREIGN PATENT DOCUMENTS

| | | |
|---|---|---|
| DE | 103 40 546 A1 | 3/2005 |
| EP | 0602730 | 6/1994 |

(Continued)

OTHER PUBLICATIONS

Kanckstedt, C. et al, "Semi-Automated 3-Dimensional Intracardiac Echocardiography: Development and Initial Clinical Experience of a New System to Guide Ablation Procedures", Heart Rhythm, 3 (12), pp. 1453-1459, 2006.

(Continued)

*Primary Examiner* — Baisakhi Roy
(74) *Attorney, Agent, or Firm* — The Small Patent Law Group; Dean D. Small (57) ABSTRACT

An embodiment of an imaging system of an imaged subject is provided. The imaging system comprises a controller, and an imaging system and a display in communication with the controller. The imaging system can include an imaging probe having a marker representative of a unique identifier. The display can be illustrative of the imaged data acquired with the imaging probe in combination with a graphic representation of an imaging plane vector representative of a general direction of a field of view (FOV) of image acquisition of the imaging probe traveling through the imaged subject.

22 Claims, 5 Drawing Sheets

(56) References Cited

U.S. PATENT DOCUMENTS

| | | | |
|---|---|---|---|
| 5,241,473 A | 8/1993 | Ishihara et al. | |
| 5,353,354 A | 10/1994 | Keller et al. | |
| 5,370,120 A | 12/1994 | Oppelt et al. | |
| 5,383,454 A | 1/1995 | Bucholz | |
| 5,391,139 A | 2/1995 | Edmundson | |
| 5,391,199 A | 2/1995 | Ben-Haim | |
| 5,409,000 A | 4/1995 | Imran | |
| 5,409,007 A | 4/1995 | Saunders et al. | |
| 5,432,544 A | 7/1995 | Ziarati | |
| 5,438,997 A | 8/1995 | Sieben et al. | |
| 5,447,154 A | 9/1995 | Cinquin et al. | |
| 5,517,990 A | 5/1996 | Kalfas et al. | |
| 5,531,520 A | 7/1996 | Grimson et al. | |
| 5,558,091 A | 9/1996 | Acker et al. | |
| 5,568,384 A | 10/1996 | Robb et al. | |
| 5,568,809 A | 10/1996 | Ben-Haim | |
| 5,579,764 A | 12/1996 | Goldreyer | |
| 5,588,432 A | 12/1996 | Crowley | |
| 5,608,849 A | 3/1997 | King | |
| 5,633,951 A | 5/1997 | Moshfeghi | |
| 5,662,108 A | 9/1997 | Budd et al. | |
| 5,682,890 A | 11/1997 | Kormos | |
| 5,687,737 A | 11/1997 | Branham et al. | |
| 5,713,946 A | 2/1998 | Ben-Haim | |
| 5,740,802 A | 4/1998 | Nafis et al. | |
| 5,765,561 A | 6/1998 | Chen et al. | |
| 5,771,895 A | 6/1998 | Slager | |
| 5,787,886 A | 8/1998 | Kelly | |
| 5,800,352 A | 9/1998 | Ferre et al. | |
| 5,810,008 A | 9/1998 | Dekel et al. | |
| 5,823,958 A | 10/1998 | Truppe | |
| 5,840,031 A | 11/1998 | Crowley | |
| 5,891,034 A | 4/1999 | Bucholz | |
| 5,924,989 A | 7/1999 | Polz | |
| 5,938,602 A | 8/1999 | Lloyd | |
| 5,957,941 A | 9/1999 | Ream | |
| 5,961,454 A | 10/1999 | Kooy et al. | |
| 5,967,980 A | 10/1999 | Ferre et al. | |
| 5,978,696 A | 11/1999 | VomLehn et al. | |
| 5,999,840 A | 12/1999 | Grimson et al. | |
| 6,006,126 A | 12/1999 | Cosman | |
| 6,016,439 A | 1/2000 | Acker | |
| 6,019,725 A | 2/2000 | Vesely et al. | |
| 6,073,043 A | 6/2000 | Schneider | |
| 6,086,532 A | 7/2000 | Panescu et al. | |
| 6,102,863 A | 8/2000 | Pflugrath et al. | |
| 6,149,592 A | 11/2000 | Yanof et al. | |
| 6,168,565 B1 | 1/2001 | Napolitano | |
| 6,200,269 B1 | 3/2001 | Lin et al. | |
| 6,203,497 B1 | 3/2001 | Dekel et al. | |
| 6,216,027 B1 | 4/2001 | Willis et al. | |
| 6,226,543 B1 | 5/2001 | Gilboa et al. | |
| 6,235,038 B1 | 5/2001 | Hunter et al. | |
| 6,246,898 B1 * | 6/2001 | Vesely et al. | 600/424 |
| 6,259,942 B1 | 7/2001 | Westermann et al. | |
| 6,259,943 B1 | 7/2001 | Cosman et al. | |
| 6,325,759 B1 | 12/2001 | Pelissier | |
| 6,351,573 B1 | 2/2002 | Schneider et al. | |
| 6,379,302 B1 | 4/2002 | Kessman et al. | |
| 6,389,311 B1 | 5/2002 | Whayne et al. | |
| 6,413,219 B1 | 7/2002 | Avila et al. | |
| 6,447,450 B1 | 9/2002 | Olstad | |
| 6,490,474 B1 | 12/2002 | Willis et al. | |
| 6,505,063 B2 | 1/2003 | Van Den Brink et al. | |
| 6,514,249 B1 | 2/2003 | Maguire et al. | |
| 6,537,217 B1 | 3/2003 | Bjaerum et al. | |
| 6,575,901 B2 | 6/2003 | Stoycos et al. | |
| 6,650,927 B1 | 11/2003 | Keidar | |
| 6,669,635 B2 | 12/2003 | Kessman et al. | |
| 6,679,847 B1 | 1/2004 | Robinson et al. | |
| 6,705,992 B2 | 3/2004 | Gatzke | |
| 6,716,166 B2 | 4/2004 | Govari | |
| 6,728,562 B1 | 4/2004 | Budd et al. | |
| 6,773,402 B2 | 8/2004 | Govari et al. | |
| 6,773,408 B1 | 8/2004 | Acker et al. | |
| 6,775,404 B1 | 8/2004 | Pagoulatos et al. | |
| 6,902,528 B1 | 6/2005 | Garibaldi et al. | |
| 6,950,689 B1 | 9/2005 | Willis et al. | |
| 7,090,639 B2 | 8/2006 | Govari | |
| 7,156,816 B2 | 1/2007 | Schwartz et al. | |
| 7,263,397 B2 | 8/2007 | Hauck et al. | |
| 7,270,634 B2 | 9/2007 | Scampini et al. | |
| 7,285,117 B2 | 10/2007 | Krueger et al. | |
| 7,314,446 B2 | 1/2008 | Byrd et al. | |
| 7,485,115 B2 | 2/2009 | Nakamura | |
| RE41,066 E | 12/2009 | Martinelli et al. | |
| 7,657,300 B2 | 2/2010 | Hunter et al. | |
| 7,775,977 B2 * | 8/2010 | Kawashima et al. | 600/437 |
| 7,844,320 B2 | 11/2010 | Shahidi | |
| 2001/0029334 A1 | 10/2001 | Graumann et al. | |
| 2002/0005719 A1 | 1/2002 | Gilboa et al. | |
| 2002/0026118 A1 | 2/2002 | Govari | |
| 2002/0042571 A1 | 4/2002 | Gilboa et al. | |
| 2003/0013958 A1 | 1/2003 | Govari et al. | |
| 2003/0045795 A1 | 3/2003 | Bjaerum et al. | |
| 2003/0074011 A1 | 4/2003 | Gilboa et al. | |
| 2003/0120318 A1 | 6/2003 | Hauck | |
| 2003/0163045 A1 | 8/2003 | Gatzke | |
| 2003/0176778 A1 | 9/2003 | Messing et al. | |
| 2003/0208102 A1 | 11/2003 | Gilboa | |
| 2004/0097805 A1 | 5/2004 | Verard | |
| 2004/0097806 A1 | 5/2004 | Hunter et al. | |
| 2004/0102769 A1 | 5/2004 | Schwartz et al. | |
| 2004/0127798 A1 | 7/2004 | Dala-Krishna et al. | |
| 2004/0138548 A1 | 7/2004 | Strommer et al. | |
| 2004/0147842 A1 | 7/2004 | Desmarais | |
| 2004/0152974 A1 | 8/2004 | Solomon | |
| 2004/0162507 A1 | 8/2004 | Govari | |
| 2004/0162550 A1 | 8/2004 | Govari et al. | |
| 2004/0249259 A1 | 12/2004 | Heimdal et al. | |
| 2004/0254458 A1 | 12/2004 | Govari | |
| 2005/0043587 A1 * | 2/2005 | Fujimori et al. | 600/160 |
| 2005/0080336 A1 | 4/2005 | Byrd et al. | |
| 2005/0090745 A1 | 4/2005 | Steen | |
| 2005/0096543 A1 | 5/2005 | Jackson et al. | |
| 2005/0131474 A1 | 6/2005 | Byrd et al. | |
| 2005/0165279 A1 | 7/2005 | Adler et al. | |
| 2005/0171428 A1 | 8/2005 | Fichtinger et al. | |
| 2005/0197557 A1 | 9/2005 | Strommer et al. | |
| 2005/0203375 A1 | 9/2005 | Willis et al. | |
| 2006/0041180 A1 | 2/2006 | Viswanathan et al. | |
| 2006/0182320 A1 | 8/2006 | Peszynski et al. | |
| 2006/0184016 A1 | 8/2006 | Glossop | |
| 2006/0229594 A1 | 10/2006 | Francischelli et al. | |
| 2006/0241445 A1 | 10/2006 | Altmann et al. | |
| 2006/0253024 A1 | 11/2006 | Altmann et al. | |
| 2006/0253029 A1 | 11/2006 | Altmann et al. | |
| 2006/0253030 A1 | 11/2006 | Altmann et al. | |
| 2006/0253031 A1 | 11/2006 | Altmann et al. | |
| 2006/0253032 A1 | 11/2006 | Altmann et al. | |
| 2006/0287890 A1 | 12/2006 | Stead et al. | |
| 2007/0130287 A1 | 6/2007 | Kumar et al. | |
| 2007/0287902 A1 | 12/2007 | Fuimaono et al. | |
| 2008/0177994 A1 | 7/2008 | Mayer | |
| 2009/0219301 A1 * | 9/2009 | Gerard et al. | 345/643 |

FOREIGN PATENT DOCUMENTS

| | | |
|---|---|---|
| EP | 1 637 070 A | 3/2005 |
| WO | 9107726 | 5/1991 |
| WO | WO 92/19157 | 11/1992 |
| WO | 9625881 | 8/1996 |
| WO | 9729682 | 8/1997 |
| WO | 9900052 | 1/1998 |
| WO | 9824065 | 6/1998 |
| WO | 9835720 | 8/1998 |
| WO | 9958055 | 11/1999 |
| WO | 0023000 | 4/2000 |
| WO | 0056215 | 9/2000 |
| WO | WO 01/20552 A1 | 3/2001 |
| WO | 0134050 | 5/2001 |

OTHER PUBLICATIONS

Proulx, T.L. et al, "Advances in Catheter-Based Ultrasound Imaging", IEEE International Ultrasonics Symposium Proceedings, 2005.

Rotger, D. et al, "Multimodal Registration of Intravascular Ultrasound Images and Angiography", Computer Vision Center Universitat Autonoma de Barcelona Bellaerra, Spain, www.cvc.uab.es/~petia/caseib2002.pdf.

Huang, X. et al, "Dynamic 3D Ultrasound and MR Image Registration of the Beating Heart", MICAI, LNCS 3750, pp. 171-178, 2005.

Martin, R. et al, "A Miniature Position and Orientation Locator for Three Dimensional Echocardiography", IEEE Proceedings on Computer in Cardiology, pp. 25-28, 1993.

Beaseley, R.A. et al, "Registration of ultrasound images", www.tgt.vanderbilt.edu/archive/registration of ultrasound images.pdf.

Leotta, D.F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Ineractive 3-D Registration of Ultrasound and Magnetic Resonance Images Based on a Magnetic Position Sensor", IEEE on Info. Tech. In Biomedicine, vol. 3, No. 4, 1999.

"Catheter Ablation", Cleveland Clinic—Heart & Vascular Institute, http://www.clevelandclinic.org/heartcenter/pub/guide/tests/procedures/ablation.htm, Apr. 2005.

Stoll, J et al, "Passive Markers for Ultrasound Tracking of Surgical Instruments", MICCAI, LNCS 3750, pp. 41-48, 2005.

Bricault Ivan et al; "Registration of Real and CT-Derived Virutal Bronchoscopic Images to Assist Transbronchial Biopsy"; IEEE Transactions on Medical Imaging, vol. 17, No. 5, Oct. 1998; 12 pgs.

"Catheter Ablation"; Heart and Vascular Institute; www.clevelandclinic.org/heartcenter; 5 pgs, Sep. 24, 2007.

Grimson W.E.L. et al; "An Automatic Registration Method for Frameless Stereotaxy, Image Guided Surgery, and Enhanced Reality Visualization": IEEE Transactions on Medical Imaging, vol. 15, No. 2, Apr. 1996; 12 pgs.

Reinhardt, H. et al; "Computer aided surgery with special focus on neuronavigation" Computerized Medical Imaging and Graphics 23(1999) 237-244; www.elsevier.com; 8 pgs.

Yamashita Juli et al; "Real-Time 3-D Model-Based Navigation System for Endoscopic Paranasal Sinus Surgery"; IEEE Transactions on Biomedical Engineering vol. 46, No. 1, Jan. 1999; 11 pgs.

Knackstedt, Christian MD et al; "Semi-automated 3-dimensional intracardiac echocardiography: Development and initial clinical experience of a new system to guide ablation procedures" 1547-5271/$—see front matter © 2006 Heart Rhythm Society; 7 pgs.

Leotta, Daniel F. et al; "Three-Dimensional Ultrasound Imaging Using Multiple Magnetic Tracking Systems and Miniature Magnetic Sensors"; IEEE Ultrasonics Symposium 1995; 4 pgs.

Lewis, Judith Thomas et al; "An Ultrasonic Approach to Localization of Fiducial Markers for Interactive, Image-Guided Neurosurgery—Part I: Principles" IEEE Transactions on Biomedical Engineering, vol. 45, No. 5, May 1998; 11 pgs.

Pagoulatos, Niko et al; "Interactive 3-D Registration of Ultrasound and Magnetic Resonance Images Based on a Magnetic Position Sensor"; IEEE Transactions on Technology in Biomedicine, vol. 3, No. 4, Dec. 1999; 11 pgs.

Roberts, David W.; "The Future of Frameless Stereotaxy"; Chapter 214, Textbook of Steriotactic and Functional Neurosurgery; McGraw-Hill 1998; 11 pgs.

St-Jean, Philippe et al; "Automated Atlas Integration and Interactive Three-Dimenstional Visualization Tools for Planning and Guidance in Functional Neurosurgery"; IEEE Transactions on Medical Imaging, vol. 17, No. 5, Oct. 1998; 9 pgs.

Proulx, T. L. et al; "Advances in Catheter-Based Ultrasound Imaging Intracardiac Echocardiography and the ACUSON AcuNav(TM) Ultrasound Catheter"; IEEE International Ultrasonics Symposium 1995; 10 pgs.

Sato, Yoshinobu Sato et al; "Image Guidance of Breast Cancer Surgery Using 3-D Ultrasound Images and Augmented Reality Visualization"; IEEE Transactions on Medical Imaging, vol. 17, No. 5, Oct. 1998, 13 pgs.

Schreiner, Steven et al; "An Ultrasonic Approach to Localization of Fiducial Markers for Interactive, Image-Guided Neurosurgery—Part II: Implementation and Automation"; IEEE Transactions on Biomedical Engineering, vol. 45, No. 5, May 1998; 11 pgs.

Stoll, Jeffrey et al; "Passive Markers for Ultrasound Tracking of Surgical Instruments"; J. Duncan and G. Gerig (Eds.): MICCAI 2005, LNCS 3750, pp. 41-48, 2005. © Springer-Verlag Berlin Heidelberg 2005; 8 pgs.

Birkfellner, Wolfgang et al; "Calibration of Tracking Systems in a Surgical Environment"; IEEE Transactions on Medical Imaging, vol. 17, No. 5, Oct. 1998; 6 pgs.

R A. Beasley,et al., Registration of Ultrasound Images, Proc. SPIE 3658. 125 (1999); doi: 10.1117/12.349423.

X. Huang, et al., Dynamic 3D Ultrasound and MR Image Registration of the Beating Heart, Medical Imaging Computing and Computer Assisted Intervention-MICCAI 2005, Lecture Notes in Computer Science 2005, vol. 3750/2005, 171-178, DOI: 10.1007/11566489_22.

Juli Yamashita, et al., Real-Time 3-D Model-Based Navigation System for Endoscopic Paranasal Sinus Surgery, IEEE Transactions on Biomedical Engineering, vol. 46, No. 1, Jan. 1999, pp. 107-116.

Office Action dated Feb. 5, 2008; U.S. Appl. No. 11/182,910, filed Jul. 15, 2008; Applicant: Donaldson et al.; 10 pages.

Office Action dated Feb. 28, 2008; U.S. Appl. No. 11/433,951, filed May 15, 2006; Applicant: Donaldson; 11 pages.

Office Action dated Jan. 16, 2008; U.S. Appl. No. 11/182,473, filed Jul. 15, 2008; Applicant: Donaldson; 11 pages.

A. Milkowski et al. "Speckle Reduction Imaging"; Technical White Paper—General Electric Health Care (Ultrasound). Last accessed on Jul. 9, 2009. Available at http:www.gehealthcare.com/usen/ultrasound/education/docs/whitepaper_SRI.pdf.

Radiology, vol. 121, 157-162, Copyright © 1976 by Radiological Society of North America.

* cited by examiner

IMAGING SYSTEM AND METHOD OF DELIVERY OF AN INSTRUMENT TO AN IMAGED SUBJECT

RELATED APPLICATIONS

This application claims priority to U.S. Provisional Application No. 60/938,290 filed on May 16, 2007, and is hereby incorporated herein by reference in its entirety.

BACKGROUND

The subject matter herein generally relates to tracking or delivery of medical instruments, and in particular, systems and methods to track and deliver medical instruments using ultrasound.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thorasoscopic surgery, endoscopic surgery, etc. Types of medical imaging systems, for example, computerized tomography (CT), magnetic resonance imaging (MRI), positron emission tomography (PET), ultrasound (US), radiological machines, etc., can be useful in providing static image guiding assistance to medical procedures. The above-described imaging systems can provide two-dimensional or three-dimensional images that can be displayed to provide a surgeon or clinician with an illustrative map to guide a tool (e.g., a catheter) through an area of interest of a patient's body.

One example of application of image-guided surgery is to perform an intervention procedure to treat cardiac disorders or arrhythmias. Heart rhythm disorders or cardiac arrhythmias are a major cause of mortality and morbidity. Atrial fibrillation is one of the most common sustained cardiac arrhythmia encountered in clinical practice. Cardiac electrophysiology has evolved into a clinical tool to diagnose these cardiac arrhythmias. As will be appreciated, during electrophysiological studies, probes, such as catheters, are positioned inside the anatomy, such as the heart, and electrical recordings are made from the different chambers of the heart.

A certain conventional image-guided surgery technique used in interventional procedures includes inserting a probe, such as an imaging catheter, into a vein, such as the femoral vein. The catheter is operable to acquire image data to monitor or treat the patient. Precise guidance of the imaging catheter from the point of entry and through the vascular structure of the patient to a desired anatomical location is progressively becoming more important. Current techniques typically employ fluoroscopic imaging to monitor and guide the imaging catheter within the vascular structure of the patient.

BRIEF SUMMARY

A technical effect of the embodiments of the system and method described herein includes enhancement in monitoring and/or treating regions of interest. Another technical effect of the subject matter described herein includes enhancement of placement and guidance of probes (e.g., catheters) traveling through an imaged subject. Yet, another technical effect of the system and method described herein includes reducing manpower, expense, and time to perform interventional procedures, thereby reducing health risks associated with long-term exposure of the subject to radiation.

According to one embodiment, an imaging system of an imaged subject is provided. The imaging system comprises a controller, and an imaging system and a display in communication with the controller. The imaging system can include an imaging probe having a marker representative of a unique identifier. The display can be illustrative of the imaged data acquired with the imaging probe in combination with a graphic representation of an imaging plane vector representative of a general direction of a field of view (FOV) of image acquisition of the imaging probe traveling through the imaged subject.

According to another embodiment of the subject matter described herein, a method of image acquisition of an imaged anatomy is provided. The method comprises the steps of: providing an imaging system including an imaging probe in communication with the controller; and acquiring an imaged data with movement of the imaging probe through the imaged subject; displaying the image data acquired with the imaging probe in combination with a graphic representation of an imaging plane vector representative of a general direction of a field of view (FOV) of image acquisition of the imaging probe traveling through the imaged subject.

Systems and methods of varying scope are described herein. In addition to the aspects of the subject matter described in this summary, further aspects of the subject matter will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
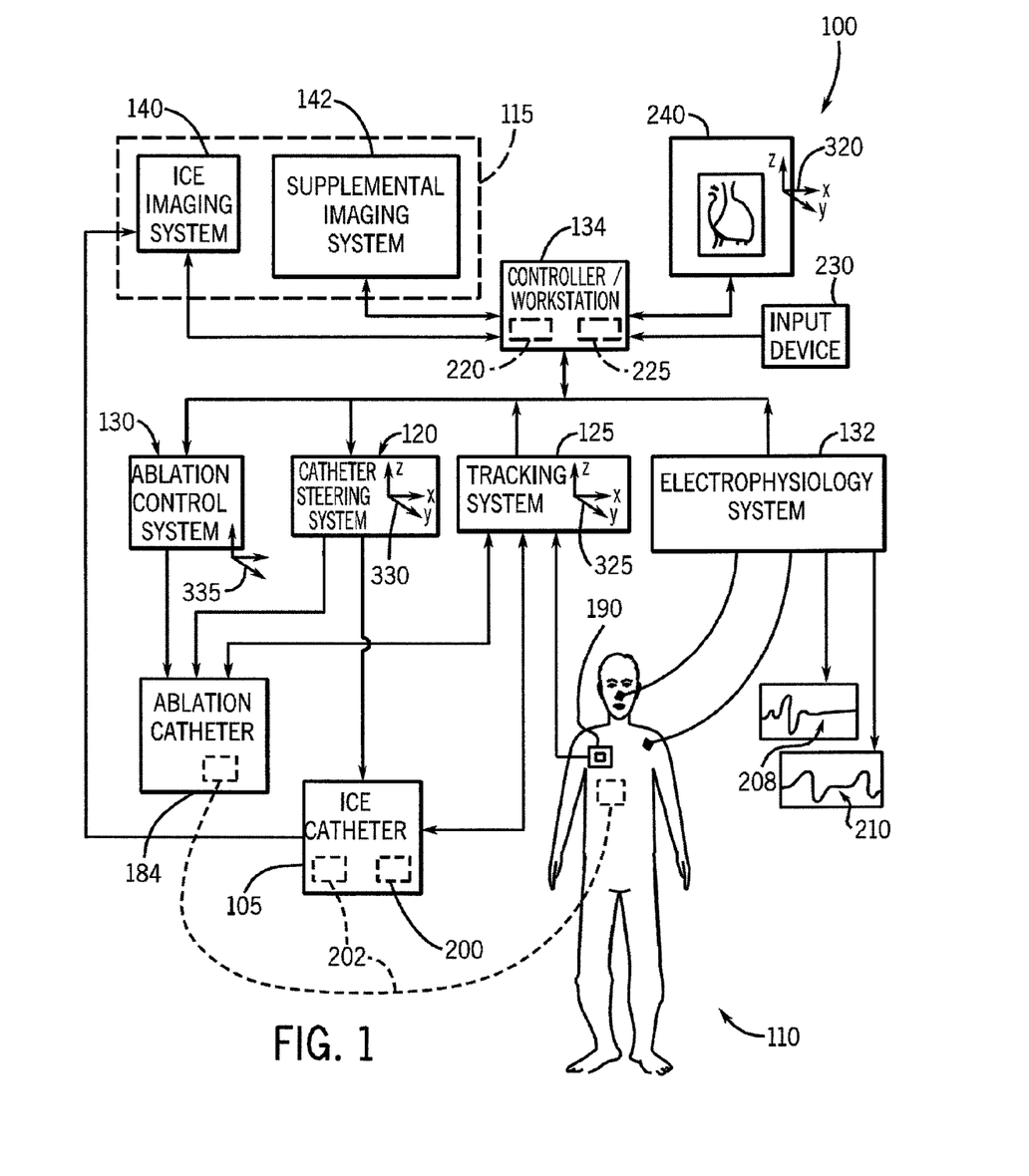
FIG. 1 illustrates a schematic diagram of an embodiment of a system of the subject matter described herein to perform imaged guided medical procedures on an imaged subject.
Figure 3:
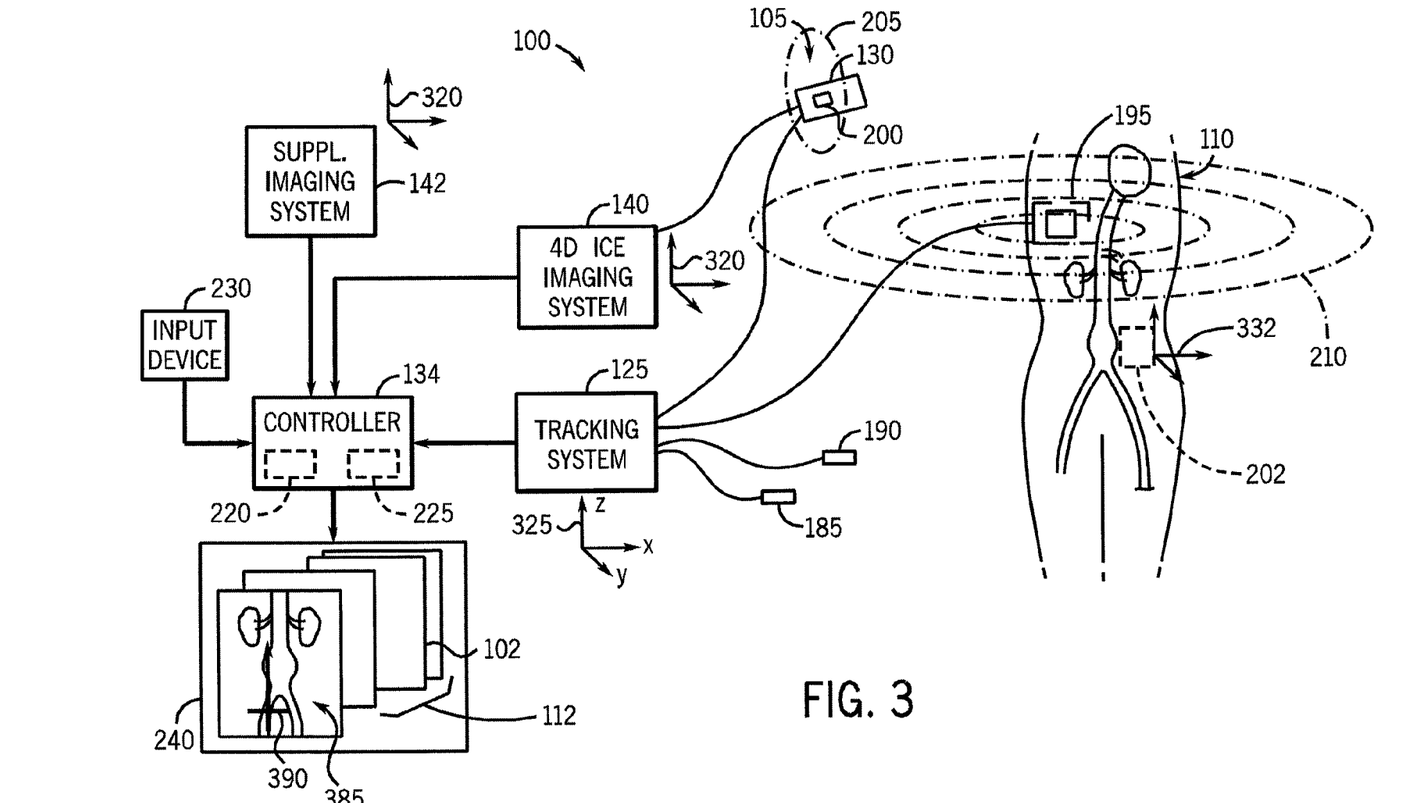
FIG. 3 illustrates a more detailed schematic diagram of a tracking system in combination with an imaging system as part of the system described in FIG. 1.

FIGS. 1 and 3 illustrate an embodiment of a system 100 operable to create a full-view three- or four-dimensional (3D or 4D) image or model from a series of generally real-time, acquired 3D or 4D image data 102 relative to a tracked position information of a probe (e.g., an imaging catheter 105) traveling through the imaged subject 110. According to one embodiment, the system 100 can be operable to acquire a series of general real-time, partial view, 3D or 4D image data 102 while simultaneously rotating and tracking a position and orientation of the catheter 105 through the imaged subject 110. From the acquired general real-time, partial views of 3D or 4D image data 102, a technical effect of the system 100 includes creating an illustration of a general real-time 3D or 4D model 112 of a region of interest (e.g., a beating heart) so as to guide a surgical procedure.

Referring to FIG. 1, an embodiment of the system 100 generally includes an image acquisition system 115, a steering system 120, a tracking system 125, an ablation system 130, and an electrophysiology system 132 (e.g., a cardiac monitor, respiratory monitor, pulse monitor, etc. or combination thereof), and a controller or workstation 134.

Referring to FIGS. 1 and 3, the image acquisition system 115 is generally operable to generate the 3D or 4D image or model 112 corresponding to an area of interest of the imaged subject 110. Examples of the image acquisition system 115 can include, but is not limited to, computed tomography (CT), magnetic resonance imaging (MRI), x-ray or radiation, positron emission tomography (PET), computerized tomosynthesis (CT), ultrasound (US), angiographic, fluoroscopic, and the like or combination thereof. The image acquisition system 115 can be operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure. Thus, the types of images acquired by the acquisition system 115 can be diagnostic or interventional.

Referring to FIGS. 1 and 3, one embodiment of the image acquisition system 115 includes a general real-time, intracardiac echocardiography (ICE) imaging system 140 that employs ultrasound to acquire general real-time, 3D or 4D ultrasound image data of the patient's anatomy and to merge the acquired image data to generate a 3D or 4D model 112 of the patient's anatomy relative to time, generating herein referred to as the 4D model or image 112. In accordance with another embodiment, the image acquisition system 115 is operable to fuse or combine acquired image data using above-described ICE imaging system 140 with pre-acquired or intra-operative image data or image models (e.g., 2D or 3D reconstructed image models) generated by another type of supplemental imaging system 142 (e.g., CT, MRI, PET, ultrasound, fluoroscopy, x-ray, etc. or combinations thereof).

Figure 2:
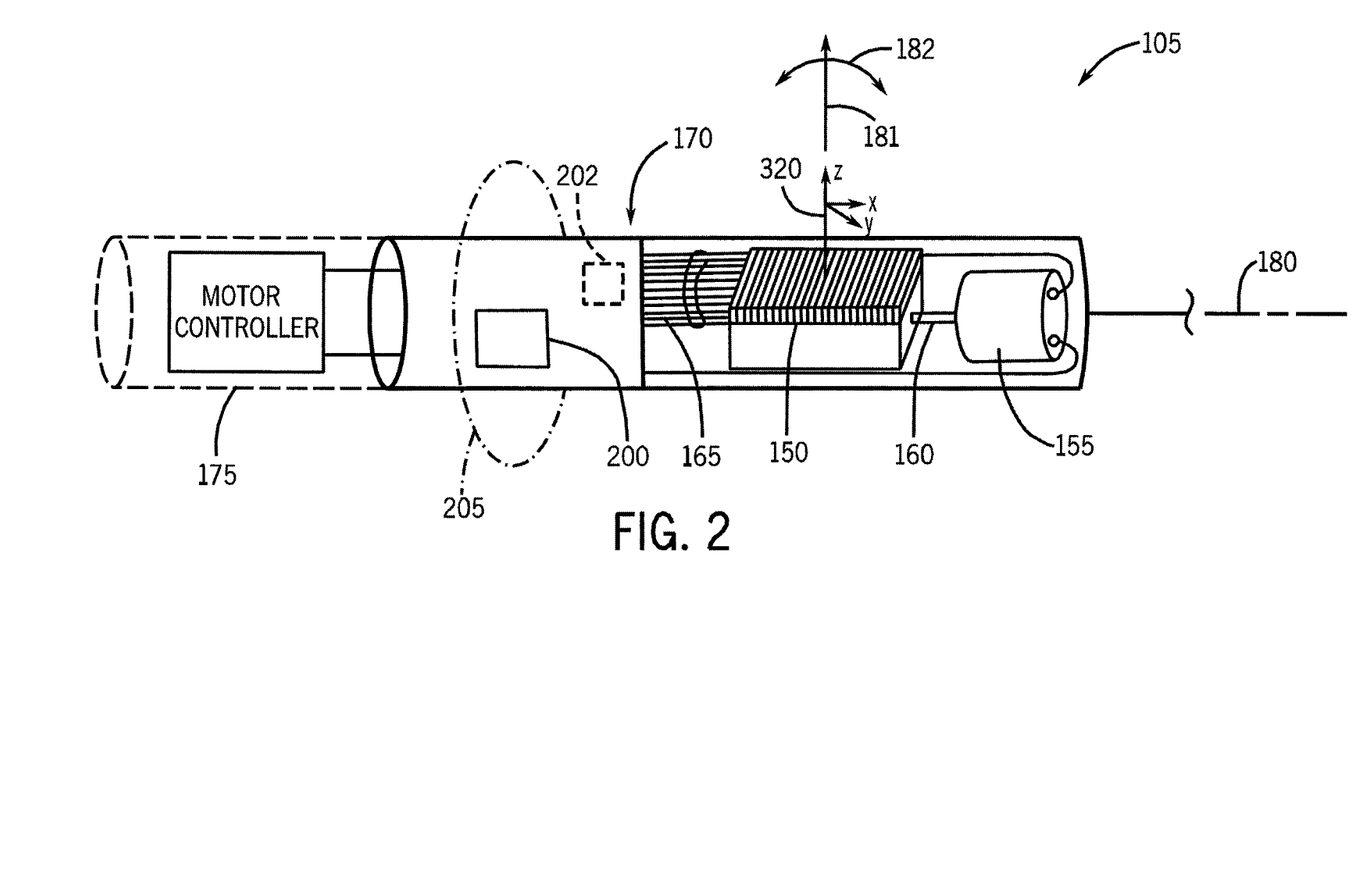
FIG. 2 illustrates a detailed schematic diagram of an embodiment of an imaging catheter of FIG. 1 to travel through the imaged subject.

FIG. 2 illustrates one embodiment of the catheter 105, herein referred to as an ICE catheter 105. The illustrated embodiment of the ICE catheter 105 includes a transducer array 150, a micromotor 155, a drive shaft or other mechanical connection 160 between the micromotor 155 and the transducer array 150, an interconnect 165, and a catheter housing 170.

According to the illustrated embodiment in FIG. 2, the micromotor 155 via the drive shaft 160 generally rotates the transducer array 150. The rotational motion of the transducer array 150 is controlled by a motor control 175 of the micromotor 155. The interconnect 165 generally refers to, for example, cables and other connections coupling so as to receive and/or transmit signals between the transducer array 150 with the ICE imaging system (shown in FIG. 1) 105. An embodiment of the interconnect 165 is configured to reduce its respective torque load on the transducer array 150 and the micromotor 155.

Still referring to FIG. 2, an embodiment of the catheter housing 170 generally encloses the transducer array 150, the micromotor 155, the drive shaft 160, and the interconnect 165. The catheter housing 170 may further enclose the motor control 175 (illustrated in dashed line). The catheter housing is generally of a material, size, and shape adaptable to internal imaging applications and insertion into regions of interest of the imaged subject 110 (See FIG. 1). At least a portion of the catheter housing 170 that intersects the ultrasound imaging volume or scanning direction is comprised of acoustically transparent (e.g., low attenuation and scattering, acoustic impedance near that of the blood and tissue (Z~1.5M Rayl) material. An embodiment of the space between the transducer array 150 and the housing 170 is filled with acoustic coupling fluid (e.g., water) having an acoustic impedance and sound velocity near those of blood and tissue (e.g., Z~1.5M Rayl, V~1540 m/sec).

An embodiment of the transducer array 150 is a 64-element one-dimensional array having 0.110 mm azimuth pitch, 2.5 mm elevation, and 6.5 MHz center frequency. The elements of the transducer array 150 are electronically phased in order to acquire a sector image generally parallel to a longitudinal axis 180 of the catheter housing 170. In operation, the micromotor 155 mechanically rotates the transducer array 150 about the longitudinal axis 180. The rotating transducer array 150 captures a plurality of two-dimensional images for transmission to the ICE imaging system 140 (shown in FIG. 1). The ICE imaging system 140 is generally operable to assemble the sequence or succession of acquired 2D images so as to generally produce or generate 3D image or reconstructed model 112 of the imaged subject 110 (See Fig.

The motor control 175 via the micromotor 155 generally regulates or controls the rate of rotation of the transducer array 150 about the longitudinal axis 180 of the ICE catheter 105. For example, the motor control 175 can instruct the micromotor 155 to rotate the transducer array 150 relatively slowly to produce the 3D reconstructed image or model 112. Also, the motor control 175 can instruct the micromotor 155 to rotate the transducer array 150 relatively faster to produce the general real-time, 3D or 4D reconstructed image or model. The 4D reconstructed image or model 112 can be defined to include a 3D reconstructed image or model correlated relative to an instant or instantaneous time of image acquisition. The motor control 175 is also generally operable to vary the direction of rotation so as to generally create an oscillatory motion of the transducer array 150. By varying the direction of rotation, the motor control 175 is operable to reduce the torque load associated with the interconnect 165, thereby enhancing the performance of the transducer array 150 to focus imaging on specific regions within the range of motion of the transducer array 150 about the longitudinal axis 180.

Referring now to FIGS. 1 through 3, an embodiment of the steering system 120 is generally coupled in communication to control maneuvering (including the position or the orientation) of the ICE catheter 105. The embodiment of the system 100 can include synchronizing the steering system 120 with gated image acquisition by the ICE imaging system 140. The steering system 120 may be provided with a manual catheter steering function or an automatic catheter steering function or combination thereof. With selection of the manual steering function, the controller 134 and/or steering system 120 aligns an imaging plane vector 181 relative to the ICE catheter 105 shown on the 3D ICE reconstructed image or model 112 per received instructions from the user, as well as directs the ICE catheter 105 to a target anatomical site. An embodiment of the imaging plane vector 181 represents a central direction of the plane that the transducer array 150 travels, moves or rotates through relative to the longitudinal axis 180. With selection of the automatic steering function, the controller 134 and/or steering system 120 or combination thereof estimates a displacement or a rotation angle 182 at or less than maximum (See FIG. 2) relative to a reference (e.g., imaging plane vector 181), passes position information of the ICE catheter 105 to the steering system 120, and automatically drives or positions the ICE catheter 105 to continuously follow movement of a second object (e.g., delivery of an ablation catheter 184 of the ablation system 130, moving anatomy, etc.). The reference (e.g., imaging plane vector 181) can vary.

Referring to FIGS. 1 and 3, the tracking system 125 is generally operable to track or detect the position of the tool or ICE catheter 105 relative to the acquired image data or 3D or 4D reconstructed image or model 112 generated by the image acquisition system 115, or relative to delivery of a second instrument or tool (e.g., ablation system 130, electrophysiology system 132).

As illustrated in FIG. 3, an embodiment of the tracking system 125 includes an array or series of microsensors or tracking elements 185, 190, 195, 200 connected (e.g., via a hard-wired or wireless connection) to communicate position data to the controller 134. Yet, it should be understood that the number of tracking elements 185, 190, 195, 200 can vary. An embodiment of the system 100 includes intraoperative tracking and guidance in the delivery of the at least one catheter 184 of the ablation system 130 (See FIG. 1) by employing a hybrid electromagnetic and ultrasound positioning technique.

An embodiment of the hybrid electromagnetic/ultrasound positioning technique can facilitate dynamic tracking by locating tracking elements or dynamic references 185, 190, 195, 200, alone in combination with ultrasound markers 202 (e.g., comprised of metallic objects such brass balls, wire, etc. arranged in unique patterns for identification purposes). The ultrasonic markers 202 may be active (e.g., illustrated in dashed line located at catheters 105 and 184) or passive targets (e.g., illustrated in dashed line at imaged anatomy of subject 110). An embodiment of the ultrasound markers 202 can be located at the ICE catheter 105 and/or ablation catheter 184 so as to be identified or detected in acquired image data by supplemental imaging system 142 and/or the ICE imaging system 140 or controller 134 or combination thereof. As image data is acquired via the ICE catheter 105, an image-processing program stored at the controller 134 or other component of the system 100 can extract or calculate a voxel position of the ultrasonic markers 202 in the image data. In this way, the controller 134 or tracking system 125 or combination thereof can track a position of the ultrasound markers 202 with respect to the ICE catheter 105, or vice versa. The tracking system 125 can be configured to selectively switch between tracking relative to electromagnetic tracking elements 185, 190, 195, 200 or ultrasound markers 202 or simultaneously track both.

For sake of example, assume the series of tracking elements 185, 190, 195, 200 includes a combination of transmitters or dynamic references 185 and 190 in communication or coupled (e.g., RF signal, optically, electromagnetically, etc.) with one or more receivers 195 and 200. The number and type transmitters in combination with receivers can vary. Either the transmitters 185 and 190 or the receivers 195 and 200 can define the reference of the spatial relation of the tracking elements 185, 190, 195, 200 relative to one another. An embodiment of one of the receivers 195 represents a dynamic reference at the imaged anatomy of the subject 110. An embodiment of the system 100 is operable to register or calibrate the location (e.g., position and/or orientation) of the tracking elements 185, 190, 195, 200 relative to the acquired imaging data by the image acquisition system 115, and operable to generate a graphic representation suitable to visualize the location of the tracking elements 185, 190, 195, 200 relative to the acquired image data.

Still referring to FIG. 3, the tracking elements 185, 190, 195, 200 generally enable a surgeon to continually track the position and orientation of the catheters 105 or 182 during surgery. The tracking elements 185, 190, 195 may be passively powered, powered by an external power source, or powered by an internal battery. One embodiment of one or more of the tracking elements or microsensors 185, 190, 195 include electromagnetic (EM) field generators having microcoils operable to generate a magnetic field, and one or more of the tracking elements 185, 190, 195, 200 include an EM field sensor operable to detect an EM field. For example, assume tracking elements 185 and 190 include a EM field sensor operable such that when positioned into proximity within the EM field generated by the other tracking elements 195 or 200 is operable to calculate or measure the position and orientation of the tracking elements 195 or 200 in real-time (e.g., continuously), or vice versa, calculate the position and orientation of the tracking elements 185 or 190.

For example, tracking elements 185 and 190 can include EM field generators attached to the subject 110 and operable to generate an EM field, and assume that tracking element 195 or 200 includes an EM sensor or array operable in combination with the EM generators 185 and 190 to generate tracking data of the tracking elements 185, 190 attached to the patient 110 relative to the microsensor 195 or 200 in real-time (e.g., continuously). According to one embodiment of the series of tracking elements 185, 190, 195, 200, one is an EM field receiver and a remainder are EM field generators. The EM field receiver may include an array having at least one coil or at least one coil pair and electronics for digitizing magnetic field measurements detected by the receiver array. It should, however, be understood that according to alternate embodiments, the number of combination of EM field receivers and EM field generators can vary.

The field measurements generated or tracked by the tracking elements 185, 190, 195, 200 can be used to calculate the position and orientation of one another and attached instruments (e.g., catheters 105 or 184 in FIG. 1) according to any suitable method or technique. An embodiment of the field measurements tracked by the combination of tracking elements 185, 190, 195, 200 are digitized into signals for transmission (e.g., wireless, or wired) to the tracking system 125 or controller 134. The controller 134 is generally operable to register the position and orientation information of the one or more tracking elements 185, 190, 195, 200 relative to the acquired imaging data from ICE imaging system 140 or other supplemental imaging system 142. Thereby, the system 100 is operable to visualized or illustrate the location of the one or more tracking elements 185, 190, 195, 200 or attached catheters 105 or 184 relative to pre-acquired image data or real-time image data acquired by the image acquisition system 115.

Still referring to FIG. 3, an embodiment of the tracking system 125 includes the tracking element 200 located at the ICE catheter 105. The tracking element 200 is in communication with the receiver 195. This embodiment of the tracking element 200 includes a transmitter that comprises a series of coils that define the orientation or alignment of the ICE catheter 105 about the rotational axis (generally aligned along the longitudinal axis 180) of the ICE catheter 105. Referring to FIG. 2, the tracking element 200 can be located integrally with the ICE catheter 105 and can be generally operable to generate or transmit an EM or magnetic field 205 to be detected by the receiver 195 of the tracking system 125. In response to passing through the magnetic field 205, the receiver 195 generates a signal representative of a spatial relation and orientation of the receiver 195 or other reference relative to the transmitter 200. Yet, it should be understood that the type or mode of coupling, link or communication (e.g., RF signal, infrared light, magnetic field, etc.) operable to measure the spatial relation varies. The spatial relation and orientation of the tracking element 200 is mechanically pre-defined or measured in relation relative to a feature (e.g., a tip) of the ICE catheter 105. Thereby, the tracking system 125 is operable to track the position and orientation of the ICE catheter 105 navigating through the imaged subject 110.

An embodiment of the tracking elements 185, 190, or 200 can include a plurality of coils (e.g., Hemholtz coils) operable to generate a magnetic gradient field to be detected by the receiver 195 of the tracking system 125 and which defines an orientation of the ICE catheter 105. The receiver 195 can include at least one conductive loop operable to generate an electric signal indicative of spatial relation and orientation relative to the magnetic field generated by the tracking elements 185, 190 and 200.

Referring back to FIG. 1, an embodiment of the ablation system 130 includes the ablation catheter 184 that is operable to work in combination with the ICE catheter 105 of the ICE imaging system 140 to delivery ablation energy to ablate or end electrical activity of tissue of the imaged subject 110. An embodiment of the ICE catheter 105 can include or be integrated with the ablation catheter 184 or be independent thereof. An embodiment of the ablation catheter 184 can include one of the tracking elements 185, 190 of the tracking system 125 described above to track or guide intra-operative delivery of ablation energy to the imaged subject 110. Alternatively or in addition, the ablation catheter 184 can include ultrasound markers 202 (illustrated in dashed line in FIG. 1) operable to be detected from the acquired ultrasound image data generated by the ICE imaging system 140. The ablation system 130 is generally operable to manage the ablation energy delivery to an ablation catheter 184 relative to the acquired image data and tracked position data.

An embodiment of an electrophysiological system(s) 132 is connected in communication with the ICE imaging system 140, and is generally operable to track or monitor or acquire data of the cardiac cycle 208 or respiratory cycle 210 of imaged subject 110. Data acquisition can be correlated to the gated acquisition or otherwise acquired image data, or correlated relative to generated 3D or 4D models 112 created by the image acquisition system 115.

Still referring FIG. 1, the controller or workstation computer 134 is generally connected in communication with and controls the image acquisition system 115 (e.g., the ICE imaging system 140 or supplemental imaging system 142), the steering system 120, the tracking system 125, the ablation system 130, and the electrophysiology system 132 so as to enable each to be in synchronization with one another and to enable the data acquired therefrom to produce or generate a full-view 3D or 4D ICE model 112 of the imaged anatomy.

An embodiment of the controller 134 includes a processor 220 in communication with a memory 225. The processor 220 can be arranged independent of or integrated with the memory 225. Although the processor 220 and memory 225 is described located the controller 134, it should be understood that the processor 220 or memory 225 or portion thereof can be located at image acquisition system 115, the steering system 120, the tracking system 125, the ablation system 130 or the electrophysiology system 132 or combination thereof.

The processor 220 is generally operable to execute the program instructions representative of acts or steps described herein and stored in the memory 225. The processor 220 can also be capable of receiving input data or information or communicating output data. Examples of the processor 220 can include a central processing unit of a desktop computer, a microprocessor, a microcontroller, or programmable logic controller (PLC), or the like or combination thereof.

An embodiment of the memory 225 generally comprises one or more computer-readable media operable to store a plurality of computer-readable program instructions for execution by the processor 220. The memory 225 can also operable to store data generated or received by the controller 134. By way of example, such media may comprise RAM, ROM, PROM, EPROM, EEPROM, Flash, CD-ROM, DVD, or other known computer-readable media or combinations thereof which can be used to carry or store desired program code in the form of instructions or data structures and which can be accessed by a general purpose or special purpose computer or other machine with a processor. When information is transferred or provided over a network or another communications connection (either hardwired, wireless, or a combination of hardwired or wireless) to a machine or remote computer, remote computer properly views the connection as a computer-readable medium. Thus, any such a connection is properly termed a computer-readable medium.

The controller 134 further includes or is in communication with an input device 230 and an output device 240. The input device 230 can be generally operable to receive and communicate information or data from user to the controller 210. The input device 230 can include a mouse device, pointer, keyboard, touch screen, microphone, or other like device or combination thereof capable of receiving a user directive. The output device 240 is generally operable to illustrate output data for viewing by the user. An embodiment of the output device 240 can be operable to simultaneously illustrate or fuse static or real-time image data generated by the image acquisition system 115 (e.g., the ICE imaging system 140 or supplemental imaging system 142) with tracking data generated by the tracking system 125. The output device 240 is capable of illustrating two-dimensional, three-dimensional image and/or four-dimensional image data or combination thereof through shading, coloring, and/or the like. Examples of the output device 240 include a cathode ray monitor, a liquid crystal display (LCD) monitor, a touch-screen monitor, a plasma monitor, or the like or combination thereof.

Having provided a description of the general construction of the system 100, the following is a description of a method 300 (see FIG. 4) of operation of the system 100 in relation to the imaged subject 110. Although an exemplary embodiment of the method 300 is discussed below, it should be understood that one or more acts or steps comprising the method 300 could be omitted or added. It should also be understood that one or more of the acts can be performed simultaneously or at least substantially simultaneously, and the sequence of the acts can vary. Furthermore, it is embodied that at least several of the following steps or acts can be represented as a series of computer-readable program instructions to be stored in the memory 225 of the controller 210 for execution by the processor 220 or one or more of the image acquisition system 115, the steering system 120, the tracking system 125, the ablation system 130, the electrophysiology system 132, or a remote computer station connected thereto via a network (wireless or wired).

Referring to FIG. 1, the controller 134 via communication with the tracking system 125 is operable to track movement of the ICE catheter 105 in accordance with known mathematical algorithms programmed as program instructions of software for execution by the processor 220 of the controller 134 or by the tracking system 125. An exemplary navigation software is INSTATRAK® as manufactured by the GENERAL ELEC- TRIC® Corporation, NAVIVISION® as manufactured by SIEMENS®, and BRAINLAB®.

Referring now to FIGS. 1 through 4, the embodiment of the method 300 includes a step of registering 310 a reference frame 320 of the ICE imaging system 140 with one or more of the group comprising: a reference frame 325 of the tracking system 125, a reference frame 330 of the steering system 120, an ultrasonic marker reference frame or coordinate system 332, a reference frame 335 of the ablation system 130, or a reference time frame of the electrophysiological system(s) (e.g., cardiac monitoring system, respiratory monitoring system, etc.) 132.

Figure 4:
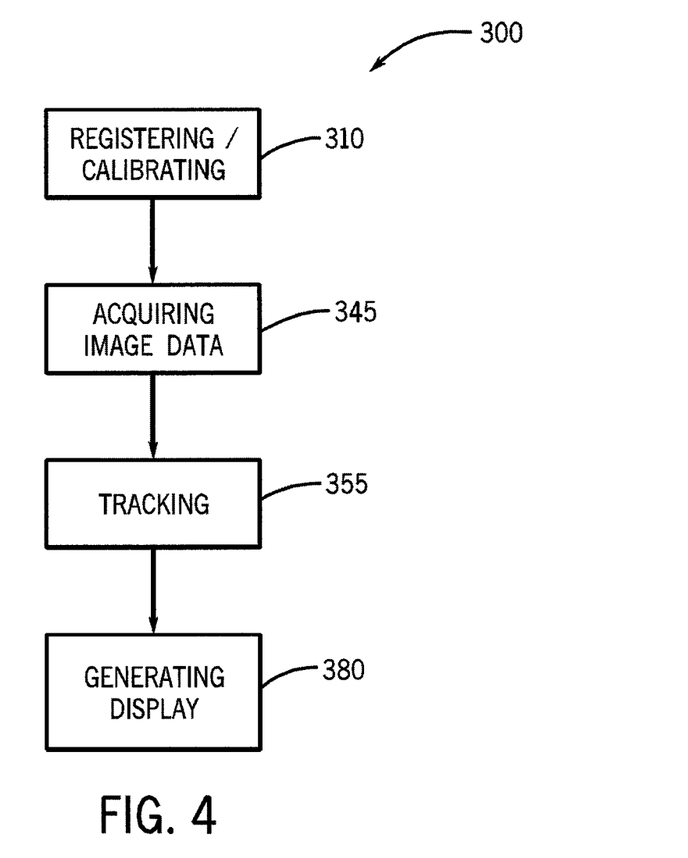
FIG. 4 shows an embodiment of a method of performing an image-guided procedure via the system of FIG. 1.
Figure 5:
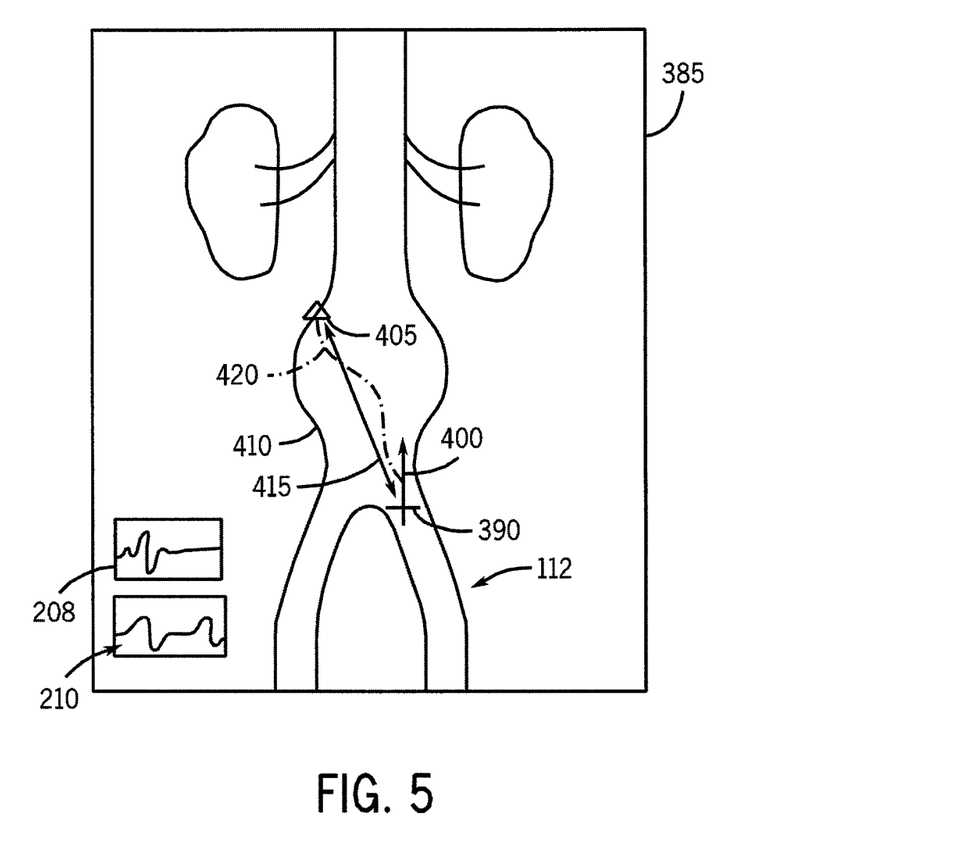
FIG. 5 shows an embodiment of an illustration of a display generated by the system of FIG. 1.

An embodiment of the method 300 further includes a step 345 of acquiring image data (e.g., scan) of the anatomy of interest of the imaged subject 110. An embodiment of the step of acquiring image data includes acquiring the series of partial-views 102 of 3D or 4D image data while rotating the ICE catheter 105 around the longitudinal axis 180. The image acquisition step 345 can include synchronizing or gating a sequence of image acquisition relative to cardiac and respiratory cycle information 208, 210 measured by the electrophysiology system 132.

The embodiment of the method 300 further includes a step 355 of tracking a position or location of the at least one catheter 105 or 184 relative to the acquired image data. According to one embodiment of the method 300, at least one catheter 105 or 184 can be integrated with one or more ultrasonic markers 202 indicative of a unique identifier. The ultrasonic markers 202 can both be located and rigidly mounted on the at least one instrument catheter 105 or 184. A computer image-processing program is operable to detect and mark positions of the ultrasonic markers 202 relative to the generated 3D or 4D ICE image model 112.

The controller 134 can be generally operable to align positions of the ultrasonic markers 202 with a tracking coordinate reference frame or coordinate system 325. This registration information may be used for the alignment (calibration) between the tracking reference frame or coordinate system 325 and the ultrasonic marker reference frame or coordinate system 332 (See FIG. 3) relative to the imaging reference frame or coordinate system 320. This information may also be used for detecting the presence of electromagnetic distortion or tracking inaccuracy.

According to one embodiment, the controller 134 can process acquired partial views of 3D or 4D image data of the catheter 105 or 184 to extract the voxel positions of the ultrasonic markers 202. The controller 134 can also process the acquired partial views of 3D or 4D image data to extract or delineate a surface model of the imaged anatomy. An embodiment of the controller 134 can also calculate at least an estimate of the imaging plane vector 181 generally representative of the central direction of the field of view of the transducer array 150 of the ICE catheter 105.

The embodiment of the ICE catheter 105 can include the tracking element 200 (e.g., electromagnetic coils or electrodes or other tracking technology) or ultrasound marker 202 operable such that the tracking system 125 can calculate the position and orientation (about six degrees of freedom) of the catheter 105. The tracking information may be used in combination with the registering step 310 described above to align the series of partial view 3D or 4D images 102 to create the larger 3D or 4D image or model 112.

According to another embodiment, the tracking system 125 may not track the position or orientation of the ICE catheter 105. The controller 134 can assemble the series of acquired partial view 3D or 4D image data 102 by matching of speckle, boundaries, and other features identified in the image data.

Referring to FIGS. 1 through 5, an embodiment of step 380 includes creating a display 385 (See FIG. 3) of the acquired real-time, partial views of 3D or 4D ICE image data 102 of the anatomical structure in combination with one or more of the following: graphic representation(s) 390 of the locations (e.g., historical, present or future or combination thereof) and identifications of the ICE catheter 105 or ablation catheter 184 relative to the acquired 3D or 4D image data or 3D or 4D models 112 generated therefrom of the imaged anatomy; a graphic representation 400 of the imaging plane vector 181 representative of a general direction of the field of view (FOV) of the ICE catheter 105; selection of a target anatomical site 405 (e.g., via input instructions from the user) at the graphically illustrated surface 410 of the generated 3D or 4D model 112 of the imaged anatomy. An embodiment of step 360 can further include creating a graphic illustration of a distance 415 between the catheter 105 (or component thereof) relative to the illustrated anatomical surface 410, a graphic illustration of a path 420 of the ICE catheter 105 or ablation catheter 184 delivery to the target anatomical site 405, or a display of the cardiac and respiratory cycles 208, 210 synchronized relative to point of time of acquisition or time of update of the displayed image data.

The technical effect of the subject matter described herein is to enable intraoperative tracking and guidance in the delivery of at least one instrument (e.g., ICE catheter 105 or ablation catheter 184) through an imaged subject 110 based on acquisition of ultrasound imaging information. According to one embodiment of the system 100 and method 300, there is no need to integrate tracking data of other navigation or tracking systems.

Embodiments of the subject matter described herein include method steps which can be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of computer program code for executing steps of the methods disclosed herein. The particular sequence of such computer- or processor-executable instructions or associated data structures represent examples of corresponding acts for implementing the functions described in such steps.

Embodiments of the subject matter described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the subject matter described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

This written description uses examples to disclose the subject matter, including the best mode, and also to enable any person skilled in the art to make and use the subject matter described herein. Accordingly, the foregoing description has been presented for purposes of illustration and description, and is not intended to be exhaustive or to limit the subject matter to the precise form disclosed, and modifications and variations are possible in light of the above teachings or may be acquired from practice of the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A tracking system comprising:
   an imaging probe configured to travel through an imaged anatomy, the imaging probe acquiring real-time three-dimensional (3D) image data of the imaged anatomy, the imaging probe configured to provide the 3D image data to an imaging system;
   an input configured to receive, from the imaging system, a 3D model of a portion of the imaged anatomy, the 3D model being generated based on the 3D image data;
   a tracking element integrated with the imaging probe to obtain real-time tracking information representative of a position of the imaging probe, the tracking information being used to generate an imaging plane vector representative of a direction of a field of view (FOV) of image acquisition of the imaging probe; and
   a controller configured to receive a graphic representation of a location of a target site relative to the imaged anatomy, generate a graphical illustration of a path of the imaging probe that leads to the target site, and map the graphic illustration of the path and the imaging plane vector onto the 3D model in real-time.

2. The system of claim 1, wherein the imaging probe includes a transducer array rotatable about a longitudinal axis of the imaging probe, the imaging probe operable to acquire ultrasound image data of the imaged subject while traveling through the imaged subject.

3. The system of claim 2, wherein the imaging probe includes a marker having a unique identifier, wherein the controller is operable to identify a location and an identification of the marker in the acquired ultrasound image data, and to generate a graphic representation of the identification and the location of the imaging probe relative to the acquired ultrasound image data for illustration in the display.

4. The system of claim 1, wherein the controller is further configured to display a graphic illustration of a distance between the imaging probe relative to an anatomical surface of the imaged anatomy of the imaged subject.

5. The system of claim 1, wherein the controller is further configured to display an illustration of a cardiac cycle or a respiratory cycle synchronized relative to a point of time of acquisition of updates continuously or periodically acquired and combined with the image data of the imaged anatomy.

6. The system of claim 1, wherein the imaging probe includes a marker having a unique identifier, wherein the marker is integrated in a construction of the imaging probe, and wherein the marker includes a metallic object representative of a unique identifier detectable in ultrasound image data acquired by the imaging probe.

7. The system of claim 1, wherein the imaging probe includes a marker, a voxel position of the marker calculated within the image data acquired by the imaging probe.

8. The system of claim 1, wherein the imaging probe includes a transducer array rotatable about a longitudinal axis of the imaging probe, the imaging plane vector extending in a direction traveled by the transducer array relative to the longitudinal axis.

9. The system of claim 1, wherein the imaging probe includes a transducer array rotatable about a longitudinal axis of the imaging probe, the transducer array acquiring sector images extending parallel to the longitudinal axis.

10. The system of claim 1, wherein the imaging probe includes a first marker having a first unique identifier and a second marker having a second unique identifier, wherein the first marker includes a plurality of metallic objects that arranged in a first pattern and the second marker includes a plurality of metallic objects that are arranged in a different second pattern.

11. The system of claim 1, further comprising an ablation catheter, the imaging catheter being configured to automatically follow a path of the ablation catheter.

12. The system of claim 1, further comprising a display co-displaying the tracking information on the 3D model of the subject.

13. A method of tracking an imaging probe, the method comprising:
   acquiring real-time three-dimensional (3D) image data of an imaged anatomy with movement of an imaging probe traveling through the imaged anatomy;
   generating a 3D model of a portion of the imaged anatomy based on the 3D image data;
   obtaining real-time tracking information representative of a position of the imaging probe;
   generating an imaging plane vector representative of a general direction of a field of view (FOV) of image acquisition of the imaging probe traveling through the imaged anatomy;
   receiving, from a user, a graphic representation of a location of a target site relative to the imaged anatomy,
   generating a graphical illustration of a path of the imaging probe that leads to the target site; and
   mapping the graphic illustration of the path and the imaging plane vector onto the 3D model in real-time.

14. The method of claim 13, wherein the step of acquiring image data includes rotating a transducer array about a longitudinal axis of the imaging probe with movement of the imaging probe through the imaged subject, the imaging probe operable to acquire ultrasound image data of the imaged subject.

15. The method of claim 14, wherein the imaging probe includes a marker representative of a unique identifier, and the method includes the steps of identifying a location and an identification of the marker in the acquired ultrasound image data, and generating a graphic representation of the identification and the location of the imaging probe relative to the acquired ultrasound image data for illustration in the display.

16. The method of claim 13, further comprising creating a graphic illustration of a distance between the imaging probe relative to an anatomical surface of the imaged anatomy of the imaged subject.

17. The method of claim 13, further comprising creating an illustration of a cardiac cycle or a respiratory cycle synchronized relative to a point of time of acquisition of updates continuously or periodically acquired and combined with the image data of the imaged anatomy.

18. The method of claim 13, wherein the imaging probe includes a marker representative of a unique identifier, wherein the marker is integrated in a construction of the imaging probe, and wherein the marker includes a metallic object representative of a unique identifier detectable in ultrasound image data acquired by the imaging probe.

19. The method of claim 13, wherein the imaging probe includes a marker, the method further comprising calculating a voxel position of the marker within the image data acquired by the imaging probe.

20. The method of claim 13, wherein the imaging plane vector extends in a direction traveled by a transducer array of the imaging probe relative to a longitudinal axis of the imaging probe.

21. The method of claim 13, wherein the imaging probe includes a transducer array rotatable about a longitudinal axis of the imaging probe, the method further comprising acquiring sector images with the transducer array, the sector images extending parallel to the longitudinal axis.

22. The method of claim 13 further comprising tracking a location of the imaging probe with a tracking system, the location of the imaging probe tracked relative to the image data acquired with the imaging probe.

* * * * *